United States Patent
Peng et al.

(10) Patent No.: US 11,486,570 B2
(45) Date of Patent: Nov. 1, 2022

(54) LIGHTING APPARATUS

(71) Applicant: XIAMEN LEEDARSON LIGHTING CO., LTD, Fujian (CN)

(72) Inventors: Pofeng Peng, Fujian (CN); TeJung Chien, Fujian (CN); Chao Wang, Fujian (CN)

(73) Assignee: XIAMEN LEEDARSON LIGHTING CO., LTD, Fujian (CN)

( * ) Notice: Subject to any disclaimer, the term of this patent is extended or adjusted under 35 U.S.C. 154(b) by 0 days.

(21) Appl. No.: 17/190,956

(22) Filed: Mar. 3, 2021

(65) Prior Publication Data

US 2021/0278077 A1    Sep. 9, 2021

(30) Foreign Application Priority Data

Mar. 3, 2020    (CN) .......................... 202020246668.5

(51) Int. Cl.
*F21V 33/00* (2006.01)
*F21V 23/04* (2006.01)
*A61L 9/20* (2006.01)
*F21V 23/06* (2006.01)

(52) U.S. Cl.
CPC ............ *F21V 33/0096* (2013.01); *A61L 9/20* (2013.01); *F21V 23/0471* (2013.01); *A61L 2209/12* (2013.01); *A61L 2209/14* (2013.01); *F21V 23/06* (2013.01)

(58) Field of Classification Search
CPC ............ F21V 33/0096; F21V 33/0092; F21V 33/0088; F21V 23/0471; F21V 23/06; F21V 29/67; F21V 29/677; F21V 7/048; F21V 7/0008; F21S 8/03; F21S 8/038; F21S 8/04; F21S 8/066; F24F 13/078; A61L 9/20; A61L 2209/12; A61L 2209/14
See application file for complete search history.

(56) References Cited

U.S. PATENT DOCUMENTS

| 4,681,024 | A  | * | 7/1987  | Ivey    | F21V 33/0092 |
|           |    |   |         |         | 362/294      |
| 2007/0243819 | A1 | * | 10/2007 | Ladanyi | F24F 13/078  |
|           |    |   |         |         | 454/354      |
| 2018/0347574 | A1 | * | 12/2018 | Niemiec | F21V 33/0092 |
| 2019/0113218 | A1 | * | 4/2019  | Wiegel  | F21V 29/76   |
| 2020/0158122 | A1 | * | 5/2020  | Huang   | F21S 8/04    |
| 2020/0306402 | A1 | * | 10/2020 | Qasem   | A61L 9/032   |

* cited by examiner

*Primary Examiner* — Y M. Quach Lee
(74) *Attorney, Agent, or Firm* — Chun-Ming Shih; Lanway IPR Services

(57) ABSTRACT

A lighting apparatus includes a fan device, a driver, a connector and a light module. The lighting apparatus is installing to a cavity of a ceiling. The fan device has a fan and an air channel. The fan is placed in the cavity. The driver converts an external power source to a first driving current supplied to the fan device. The connector is fixed to the fan device. The first light source receives a second driving current provided by the driver. The air channel has an entrance between the main housing and the fan device. The entrance is visually concealed by the main housing when a viewer stands below the lighting apparatus.

17 Claims, 9 Drawing Sheets

LIGHTING APPARATUS

FIELD

The present invention is related to a lighting apparatus, and more particularly related to a lighting apparatus with an air processing function.

BACKGROUND

The time when the darkness is being lighten up by the light, human have noticed the need of lighting up this planet. Light has become one of the necessities we live with through the day and the night. During the darkness after sunset, there is no natural light, and human have been finding ways to light up the darkness with artificial light. From a torch, candles to the light we have nowadays, the use of light have been changed through decades and the development of lighting continues on.

Early human found the control of fire which is a turning point of the human history. Fire provides light to bright up the darkness that have allowed human activities to continue into the darker and colder hour of the hour after sunset. Fire gives human beings the first form of light and heat to cook food, make tools, have heat to live through cold winter and lighting to see in the dark.

Lighting is now not to be limited just for providing the light we need, but it is also for setting up the mood and atmosphere being created for an area. Proper lighting for an area needs a good combination of daylight conditions and artificial lights. There are many ways to improve lighting in a better cost and energy saving. LED lighting, a solid-state lamp that uses light-emitting diodes as the source of light, is a solution when it comes to energy-efficient lighting. LED lighting provides lower cost, energy saving and longer life span.

The major use of the light emitting diodes is for illumination. The light emitting diodes is recently used in light bulb, light strip or light tube for a longer lifetime and a lower energy consumption of the light. The light emitting diodes shows a new type of illumination which brings more convenience to our lives. Nowadays, light emitting diode light may be often seen in the market with various forms and affordable prices.

After the invention of LEDs, the neon indicator and incandescent lamps are gradually replaced. However, the cost of initial commercial LEDs was extremely high, making them rare to be applied for practical use. Also, LEDs only illuminated red light at early stage. The brightness of the light only could be used as indicator for it was too dark to illuminate an area. Unlike modern LEDs which are bound in transparent plastic cases, LEDs in early stage were packed in metal cases.

In 1878, Thomas Edison tried to make a usable light bulb after experimenting different materials. In November 1879, Edison filed a patent for an electric lamp with a carbon filament and keep testing to find the perfect filament for his light bulb. The highest melting point of any chemical element, tungsten, was known by Edison to be an excellent material for light bulb filaments, but the machinery needed to produce super-fine tungsten wire was not available in the late 19th century. Tungsten is still the primary material used in incandescent bulb filaments today.

Early candles were made in China in about 200 BC from whale fat and rice paper wick. They were made from other materials through time, like tallow, spermaceti, colza oil and beeswax until the discovery of paraffin wax which made production of candles cheap and affordable to everyone. Wick was also improved over time that made from paper, cotton, hemp and flax with different times and ways of burning. Although not a major light source now, candles are still here as decorative items and a light source in emergency situations. They are used for celebrations such as birthdays, religious rituals, for making atmosphere and as a decor.

Illumination has been improved throughout the times. Even now, the lighting device we used today are still being improved. From the illumination of the sun to the time when human can control fire for providing illumination which changed human history, we have been improving the lighting source for a better efficiency and sense. From the invention of candle, gas lamp, electric carbon arc lamp, kerosene lamp, light bulb, fluorescent lamp to LED lamp, the improvement of illumination shows the necessity of light in human lives.

There are various types of lighting apparatuses. When cost and light efficiency of LED have shown great effect compared with traditional lighting devices, people look for even better light output. It is important to recognize factors that can bring more satisfaction and light quality and flexibility.

It is useful to add enhanced functions to light devices. When a light device is installed to a ceiling, it occupies a great position for providing functions.

Therefore, it is helpful for enhance the design of such light devices and beneficial to find a reliable design to add values to light devices.

SUMMARY

In some embodiments, a lighting apparatus includes a fan device, a driver, a connector, and a light module.

The lighting apparatus is installing to a cavity of a ceiling.

The fan device has a fan and an air channel. The fan is placed in the cavity.

The driver converts an external power source to a first driving current supplied to the fan device.

The connector is fixed to the fan device. In some embodiments, the connector also has a fixing unit to fix to the ceiling. For example, the connector may have two elastic levers to fix to the cavity of the ceiling. In some other embodiments, the connector may have screw holes to be fixed to the ceiling.

The light module having a top cover, a main container and a first light source.

The top housing is attached to the connector.

The main container is fixed to the top cover and has a light opening for a first light emitted by the first light source to escape.

The main housing is exposed outside the cavity. Specifically, the fan device is hidden inside the cavity of the ceiling while the light module is at least partially exposed outside the cavity.

The first light source receives a second driving current provided by the driver.

The air channel has an entrance between the main housing and the fan device. The entrance is visually concealed by the main housing when a viewer stands below the lighting apparatus.

In some embodiments, the connector has a power electrode for providing a second driving current to the first light source.

In some embodiments, the driver is integrated with the fan device and the first light source receives the second driving current via the power electrode.

The second driving current is a direct current power.

In some embodiments, the light module is detachable from the connector to be replaced with another light module.

In some embodiments, the connector has a track for a connector part of the top cover to slide in, and the power electrode engages electrically with the first light source when the connector part of the top cover is moved to a predetermined position of the track.

In some embodiments, the connector has an Edison socket, and the top cover of the light module has an Edison cap to be attached to the Edison socket.

In some embodiments, the light module has an extending plate and a second light source.

The second light source receives a third driving power from the driver to emit a second reflected light reflected by the extending plate.

In some embodiments, the extending plate has a prism surface with multiple protruding reflecting units.

In some embodiments, the extending plate conceals a lateral side of the connector and leaves another lateral side of the connector kept open as the entrance of the air channel.

In some embodiments, a motion sensor is disposed on the extending plate facing downwardly to a ground for detecting whether there is a person movement and the driver is electrically connected to the motion sensor to determine a response according to the person movement.

In some embodiments, the second light source is turned off when the first light source is turned on.

In some embodiments, the entrance is disposed between the fan device and the top cover of the light module with a air entrance direction having an angle less than 30 degrees with respect to a surface of the ceiling.

In some embodiments, the fan device has a filter for filtering dust of an air flowing via the entrance of the air channel.

In some embodiments, a third light source is disposed in the air channel to sanitize an air passing by the air channel.

The third light source has an ultraviolet light.

In some embodiments, the ultraviolet light emits a third light with a wave length between 100 to 180 nm.

The third light source is concealed within the air channel and the third light is not exposed outside the lighting device.

In some embodiments, an ultra incense device is disposed in the air channel to transmit an artificial odor.

In some embodiments, the fan device has a heater for generated a heated air outside the entrance of the air channel.

In some embodiments, the light module has a heat sink thermally connected to the first light source to transmit heat of the first light source to engage the air channel for heat dissipation.

In some embodiments, the fan device has a housing made with a single folded metal sheet.

In some embodiments, the first light source is arranged as a ring surrounding a filter facing to the entrance of the air channel.

DETAILED DESCRIPTION

Figure 5:
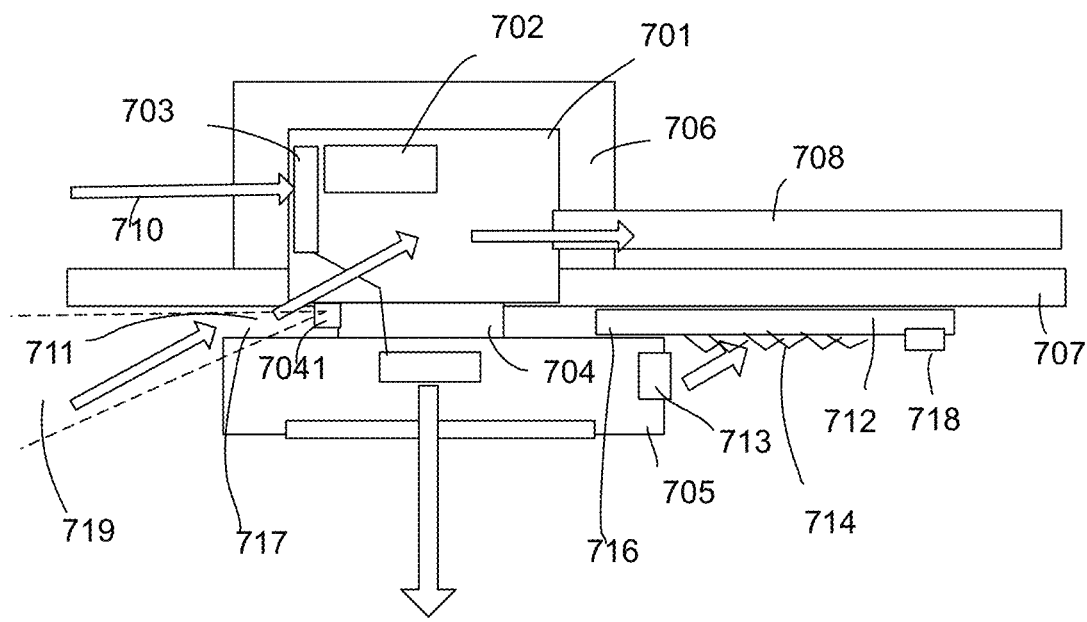
FIG. 5 illustrates another lighting apparatus embodiment.
Figure 5:
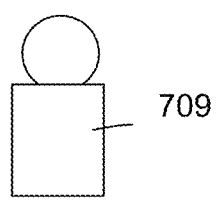

In FIG. 5, a lighting apparatus includes a fan device 701, a driver 703, a connector 704 and a light module 705.

The lighting apparatus is installing to a cavity 706 of a ceiling 707.

The fan device 701 has a fan 702 and an air channel 708. The air channel 708 may include multiple segments. Air may be brought into the cavity and moving to outside of a room or may be carried from outside to enter the room via the air channel 708.

The fan device 701 is placed in the cavity 706. In some embodiments, the ceiling is flat and the fan device 701 is concealed visually by the light module 705 when a viewer 709 stands below the lighting apparatus.

The driver 703 converts an external power source 710 to a first driving current (not illustrated, an invisible electrical component) supplied to the fan device 701.

The connector 704 is fixed to the fan device 701. In some embodiments, the connector 704 also has a fixing unit 7041 to fix to the ceiling. For example in FIG. 4, the connector 704 may have two elastic levers 2041 to fix to the cavity of the ceiling. In some other embodiments, the connector may have screw holes to be fixed to the ceiling. Other fixing units may be used for fitting different installation environment.

Figure 8:
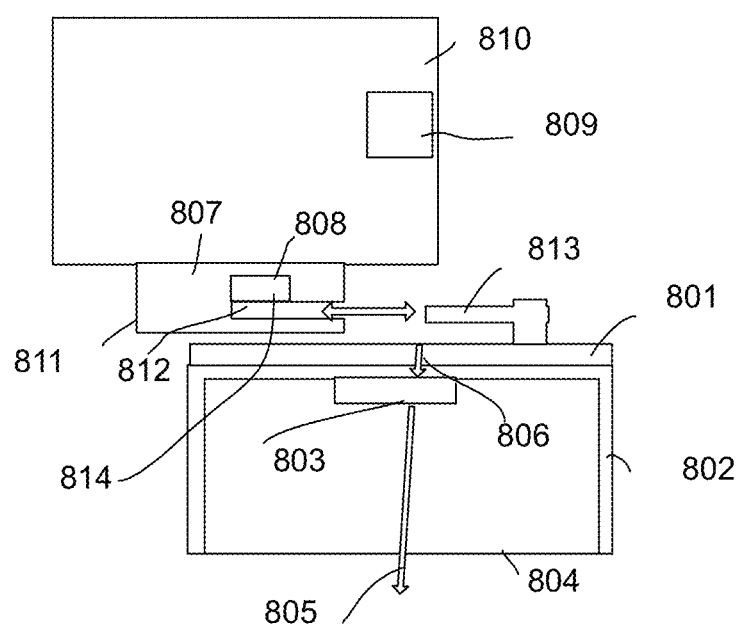
FIG. 8 shows a detachable design.

In FIG. 8, the light module has a top cover 801, a main container 802 and a first light source 803.

The top housing is attached to the connector.

The main container 802 is fixed to the top cover 801 and has a light opening 804 for a first light 805 emitted by the first light source 803 to escape.

The main container 802 is exposed outside the cavity. Specifically, the fan device is hidden inside the cavity of the ceiling while the light module is at least partially exposed outside the cavity. In some embodiments, the light module may be embedded into a cavity of a ceiling.

The first light source receives a second driving current 806 provided by the driver.

In FIG. 5, the air channel 708 has an entrance 711 between the light module 705 and the fan device 701. The entrance is visually concealed by the main housing when a viewer stands below the lighting apparatus.

In FIG. 8, the connector 807 has a power electrode 808 for providing a second driving current 806 to the first light source.

In some embodiments, the driver 809 is integrated with the fan device 810 and the first light source receives the second driving current via the power electrode 808.

The second driving current is a direct current power. In other words, the driver 809 converts an AC power to a DC power supplied to the first light source 803.

In some embodiments, the light module is detachable from the connector to be replaced with another light module.

In some embodiments, the connector 811 has a track 812 for a connector part 813 of the top cover 8101 to slide in, and the power electrode 808 engages electrically with the first light source 803 when the connector part 813 of the top cover 801 is moved to a predetermined position 814 of the track 812.

Figure 9:
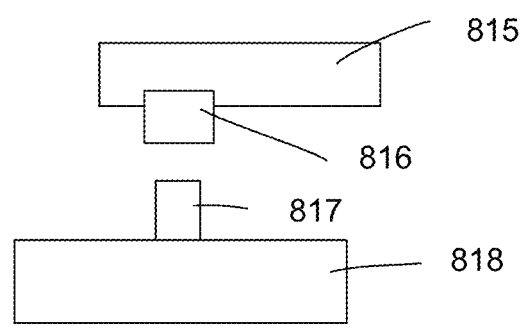
FIG. 9 shows another arrangement of a lighting apparatus.

In FIG. 9, the connector 815 has an Edison socket 816, and the top cover of the light module 818 has an Edison cap 817 to be attached to the Edison socket 816. The light module may be a flat light device, not a traditional light bulb.

In FIG. 5, the light module has an extending plate 712 and a second light source 713.

The second light source 713 receives a third driving power from the driver to emit a second light reflected by the extending plate 712.

In some embodiments, the extending plate 712 has a prism surface 714 with multiple protruding reflecting units.

In some embodiments, the extending plate conceals a lateral side 716 of the connector and leaves another lateral side 717 of the connector kept open as the entrance of the air channel.

In some embodiments, a motion sensor is disposed on the extending plate facing downwardly to a ground for detecting whether there is a person movement and the driver is electrically connected to the motion sensor 718 to determine a response according to the person movement.

In some embodiments, the second light source is turned off when the first light source is turned on.

In some embodiments, the entrance is disposed between the fan device and the top cover of the light module with a air entrance direction having an angle 719 less than 30 degrees with respect to a surface of the ceiling.

Figure 7:
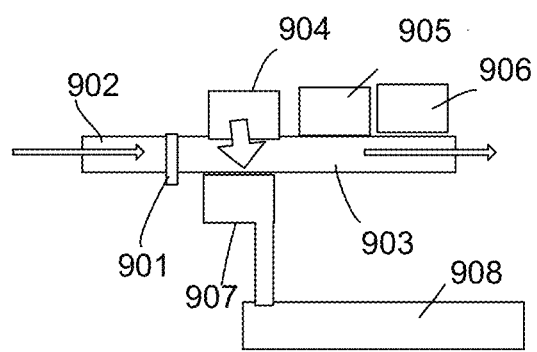
FIG. 7 shows adding enhanced units to the lighting apparatus.

In FIG. 7, the fan device has a filter 901 for filtering dust of an air flowing via the entrance 902 of the air channel 903.

In some embodiments, a third light source 904 is disposed in the air channel 903 to sanitize an air passing by the air channel 903.

The third light source has an ultraviolet light.

In some embodiments, the ultraviolet light emits a third light with a wave length between 100 to 180 nm.

The third light source is concealed within the air channel and the third light is not exposed outside the lighting device.

In some embodiments, an ultra-sound incense device 905 is disposed in the air channel to transmit an artificial odor. For example, an ultra-sound device excites water with incense device to vaporize as air.

In some embodiments, the fan device has a heater 906 for generated a heated air outside the entrance of the air channel.

In some embodiments, the light module has a heat sink 907 thermally connected to the first light source 908 to transmit heat of the first light source 908 to engage the air channel for heat dissipation.

Figure 6:
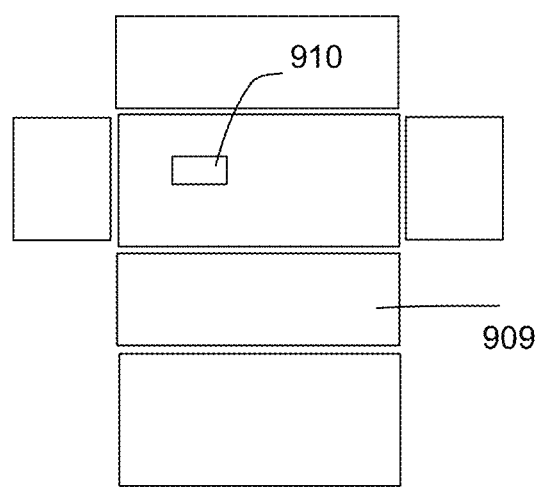
FIG. 6 shows a component of a fan device.

In FIG. 6, the fan device has a housing made with a single folded metal sheet 909. FIG. 6 illustrates an unfolded metal sheet to be folded as a box with a connector 910 for fixing a fan.

Figure 10:
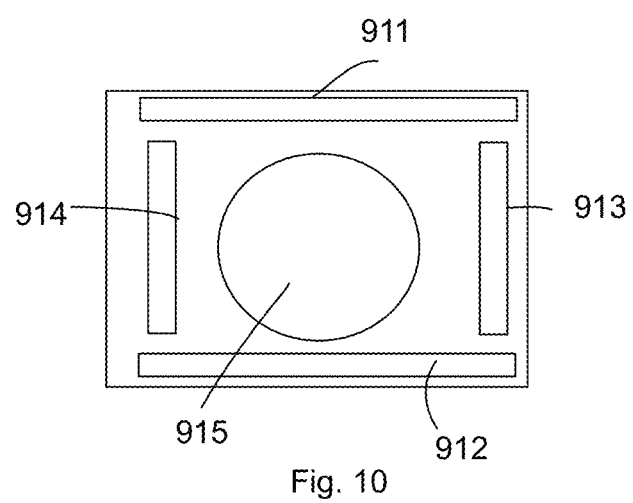
FIG. 10 shows another design of an embodiment.

In FIG. 10, the first light source, which has four light strips 911, 912, 913, 914 as an example, is arranged as a ring surrounding a filter 915 facing to the entrance of the air channel.

Figure 1:
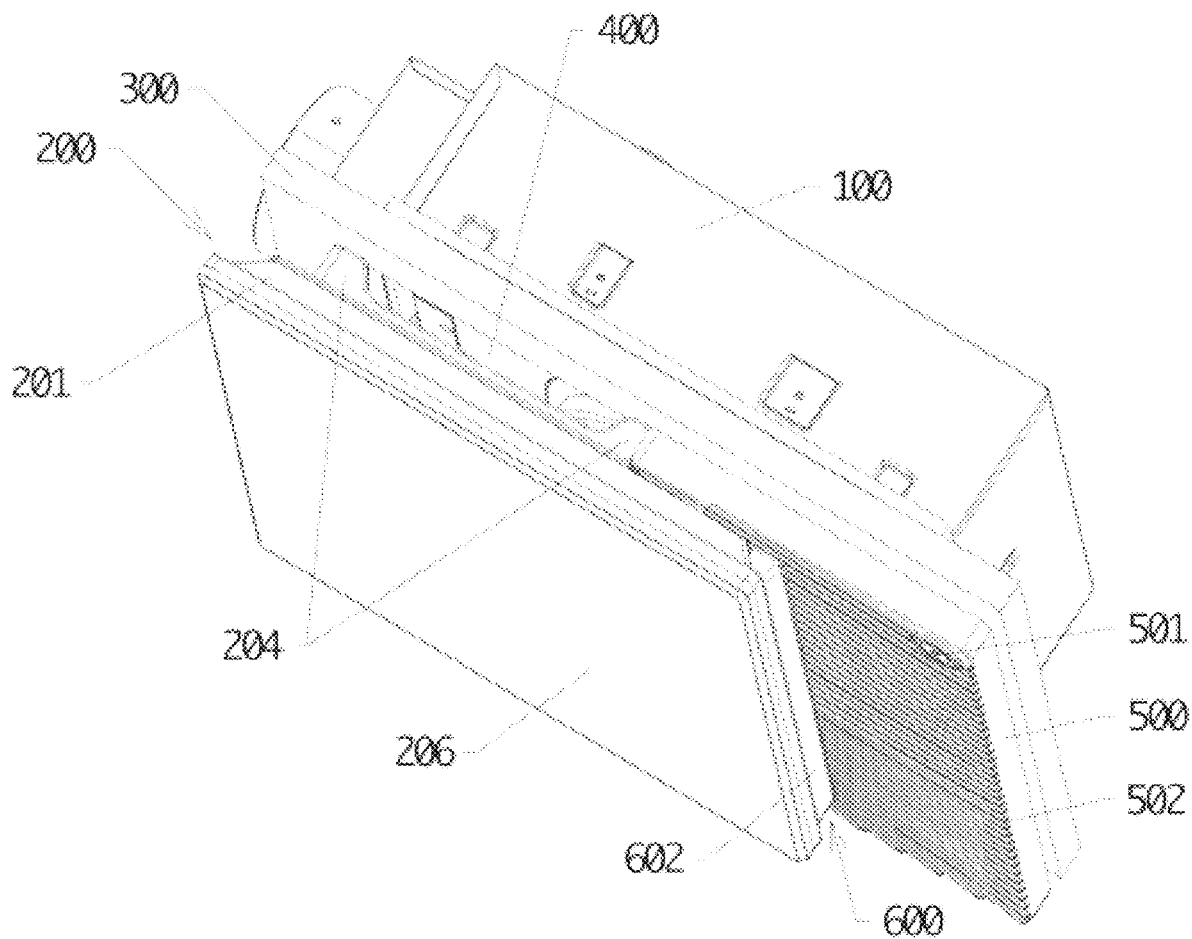
FIG. 1 illustrates a lighting apparatus embodiment.

Please refer to FIG. 1, which illustrates a lighting apparatus embodiment.

In FIG. 1, the lighting apparatus has an entrance 400 for air to entering an air channel. There is a motion sensor 501 disposed on an extending plate 500, which has multiple protruding structures 502 for reflecting light from a second light source 600.

There is a shield 602 that is used for protecting the second light source 600 but allows light to pass through.

A light passing cover 206 is disposed on a light module 200. The light module is connected to a fan device 100 via a connector 204. The light module 200 has a main container 201.

Figure 2:
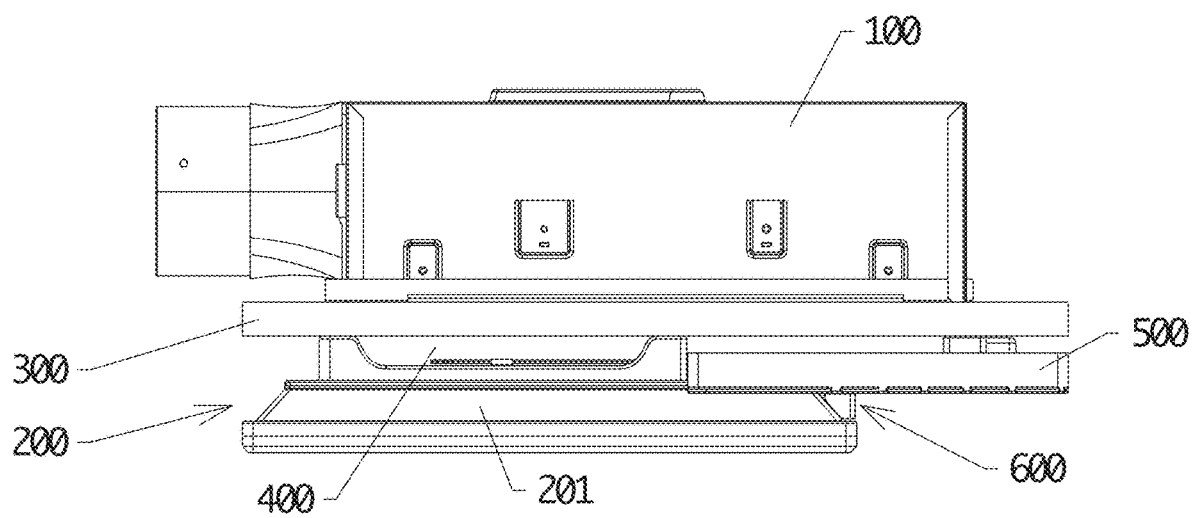
FIG. 2 illustrates a side view of the example in FIG. 1.

FIG. 2 shows a side view of the example in FIG. 1.

In FIG. 2, the ceiling 300 if further illustrated to show the relation among the components of the lighting apparatus and how these components are disposed with respect to the ceiling 300.

Figure 3:
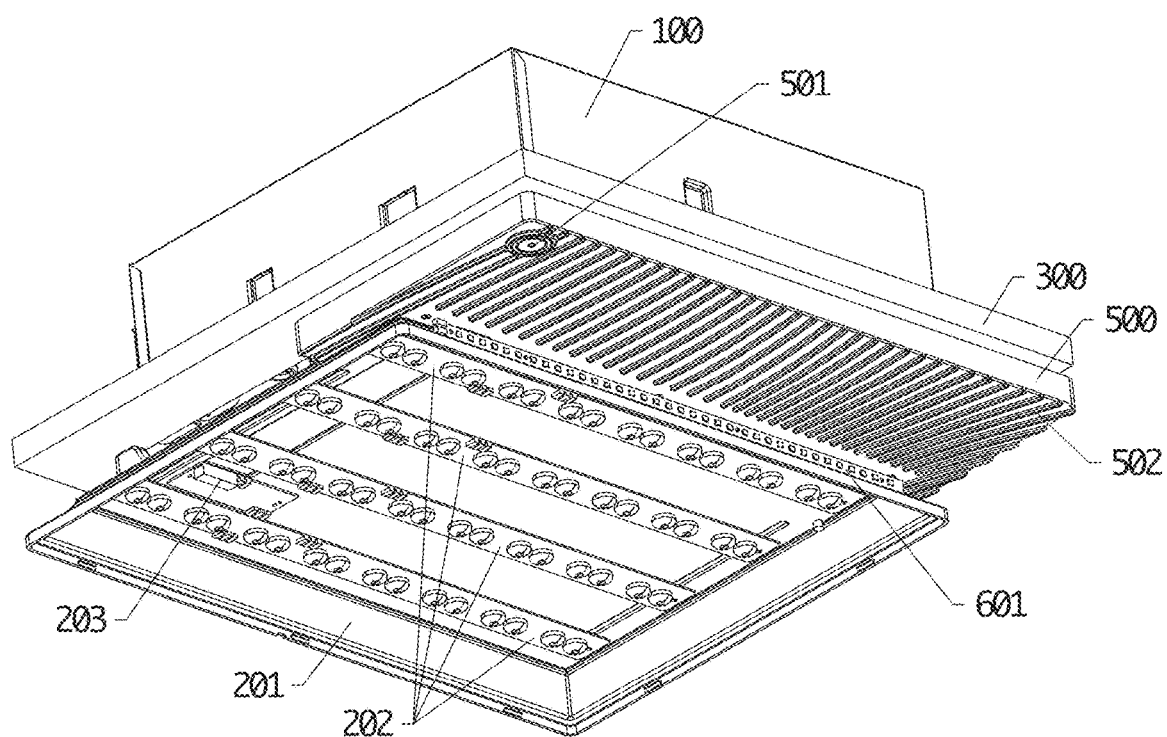
FIG. 3 illustrates a diagram showing inner components of the example of FIG. 1.

FIG. 3 further shows the details of the example in FIG. 1.

In FIG. 3, the protruding bars 502 are used for reflecting lights of the second light strip 601 of the second light source.

The first light source has multiple light strips 202 disposed to a housing 201. A driver 203 is integrated in the light module.

Figure 4:
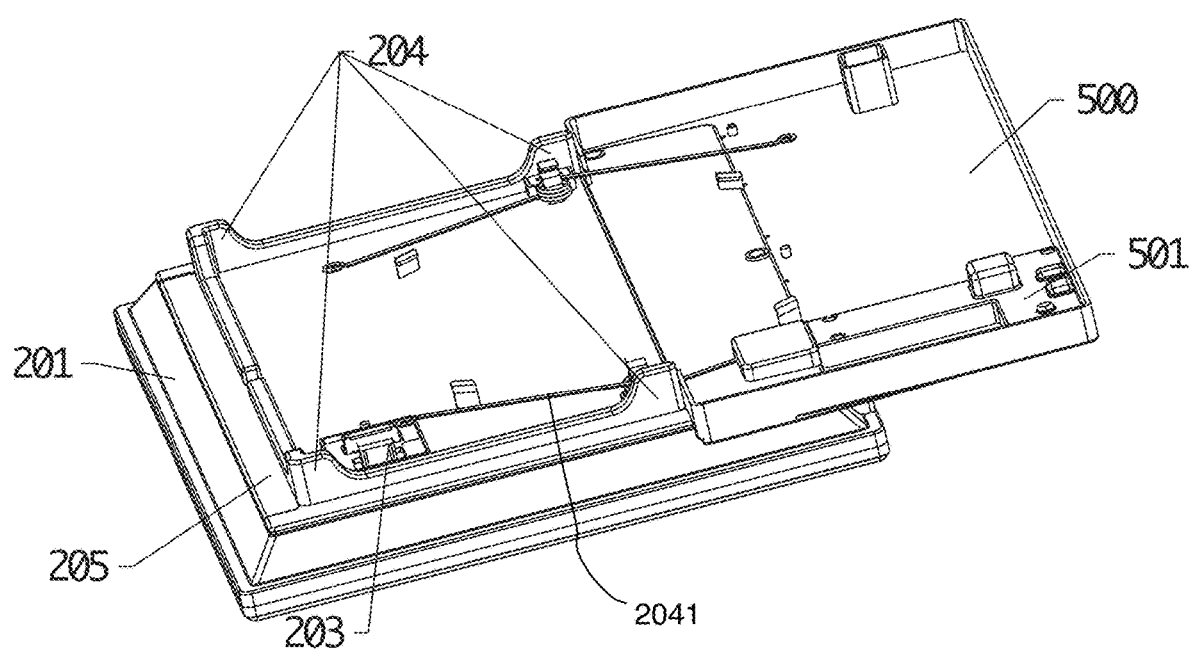
FIG. 4 illustrates a back view of the lighting apparatus of FIG. 1.

FIG. 4 shows a top view of the lighting apparatus in FIG. 1.

In FIG. 4, the connector part 204 of the top cover is further illustrated to fix to a connector of the fan device. There is a protruding platform to keep air entrance gap for air to move in or move out.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings.

The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. A lighting apparatus for installing to a cavity of a ceiling, comprising:
   a fan device having a fan and an air channel, wherein the fan is placed in the cavity;
   a driver for converting an external power source to a first driving current supplied to the fan device;
   a connector fixed to the fan device; and
   a light module having a top cover, a main container and a first light source, wherein the top housing is attached to the connector, the main container is fixed to the top cover and has a light opening for a first light emitted by the first light source to escape, the main container is exposed outside the cavity, the first light source receives a second driving current provided by the driver, wherein the air channel has an entrance between the light module and the fan device, the entrance is visually concealed by the main housing when a viewer stands below the lighting apparatus, wherein the connector has a power electrode for providing a second driving current to the first light source, wherein the connector has an Edison socket, and the top cover of the light module has an Edison cap to be attached to the Edison socket.

2. The lighting apparatus of claim 1, wherein the driver is integrated with the fan device and the first light source receives the second driving current via the power electrode, the second driving current is a direct current power.

3. The lighting apparatus of claim 1, wherein the light module is detachable from the connector to be replaced with another light module.

4. The lighting apparatus of claim 3, wherein the connector has a track for a connector part of the top cover to slide in, and the power electrode engages electrically with the first light source when the connector part of the top cover is moved to a predetermined position of the track.

5. The lighting apparatus of claim 1, wherein the light module has an extending plate and a second light source, the second light source receives a third driving power from the driver to emit a second reflected light reflected by the extending plate.

6. The lighting apparatus of claim 5, wherein the extending plate has a prism surface with multiple protruding reflecting units.

7. The lighting apparatus of claim 5, wherein the extending plate conceals a lateral side of the connector and leaves another lateral side of the connector kept open as the entrance of the air channel.

8. The lighting apparatus of claim 5, wherein a motion sensor is disposed on the extending plate facing downwardly to a ground for detecting whether there is a person movement and the driver is electrically connected to the motion sensor to determine a response according to the person movement.

9. The lighting apparatus of claim 8, wherein the second light source is turned off when the first light source is turned on.

10. The lighting apparatus of claim 5, wherein the entrance is disposed between the fan device and the top cover of the light module with a air entrance direction having an angle less than 30 degrees with respect to a surface of the ceiling.

11. The lighting apparatus of claim 1, wherein the fan device has a filter for filtering dust of an air flowing via the entrance of the air channel.

12. The lighting apparatus of claim 1, wherein a second light source is disposed in the air channel to sanitize an air passing by the air channel, the third light source has an ultraviolet light.

13. The lighting apparatus of claim 12, wherein the ultraviolet light emits a third light with a wave length between 100 to 180 nm, the second light source is concealed within the air channel and the third light is not exposed outside the lighting device.

14. The lighting apparatus of claim 1, wherein an ultra incense device is disposed in the air channel to transmit an artificial odor.

15. The lighting apparatus of claim 1, wherein the light module has a heat sink thermally connected to the first light source to transmit heat of the first light source to engage the air channel for heat dissipation.

16. The lighting apparatus of claim 1, wherein the fan device has a housing made with a single folded metal sheet.

17. The lighting apparatus of claim 1, wherein the first light source is arranged as a ring surrounding a filter facing to the entrance of the air channel.

* * * * *